US009265277B2

(12) United States Patent
Gellenbeck et al.

(10) Patent No.: US 9,265,277 B2
(45) Date of Patent: Feb. 23, 2016

(54) MULTICAROTENOID BEADLETS AND RELATED METHOD

(75) Inventors: Kevin W. Gellenbeck, Poway, CA (US); Dawna Salter Venzon, Arcadia, CA (US); Amitabh Chandra, Ada, MI (US); Janjira Intra, La Habra, CA (US); Kerry A. Grann, Lansing, MI (US)

(73) Assignee: ACCESS BUSINESS GROUP INTERNATIONAL LLC, Ada, MI (US)

( * ) Notice: Subject to any disclaimer, the term of this patent is extended or adjusted under 35 U.S.C. 154(b) by 865 days.

(21) Appl. No.: 13/548,604

(22) Filed: Jul. 13, 2012

(65) Prior Publication Data
US 2013/0017292 A1 Jan. 17, 2013

Related U.S. Application Data

(60) Provisional application No. 61/508,116, filed on Jul. 15, 2011.

(51) Int. Cl.
| | |
|---|---|
| *A23L 1/00* | (2006.01) |
| *A23L 1/275* | (2006.01) |
| *A23L 1/303* | (2006.01) |
| *A61K 31/07* | (2006.01) |
| *A61K 31/122* | (2006.01) |
| *A61K 9/50* | (2006.01) |
| *A61K 31/01* | (2006.01) |
| *A61K 31/015* | (2006.01) |
| *A61K 31/047* | (2006.01) |

(52) U.S. Cl.
CPC ............... *A23L 1/303* (2013.01); *A23L 1/0029* (2013.01); *A23L 1/2753* (2013.01); *A23V 2002/00* (2013.01); *A61K 9/5073* (2013.01); *A61K 31/01* (2013.01); *A61K 31/015* (2013.01); *A61K 31/047* (2013.01); *A61K 31/07* (2013.01); *A61K 31/122* (2013.01)

(58) Field of Classification Search
CPC ..... A23L 1/0029; A23L 1/2753; A23L 1/303; A23V 2002/00; A23V 2250/211; A23V 2250/213; A61K 9/5078; A61K 31/01; A61K 31/07; A61K 31/122
See application file for complete search history.

(56) References Cited

U.S. PATENT DOCUMENTS

| | | |
|---|---|---|
| 2005/0095301 A1 | 5/2005 | Deshpande |
| 2010/0112188 A1 | 5/2010 | Deshpande |

FOREIGN PATENT DOCUMENTS

| | | |
|---|---|---|
| AU | 2002348718 | 12/2003 |
| CN | 1205690 | 1/1999 |
| CN | 101292965 | 10/2008 |
| CN | 201719567 | 1/2011 |
| EP | 1513804 | 12/2003 |
| IN | 2181/MUM/2007 | 1/2007 |
| JP | 2010-159276 | 7/2010 |
| WO | 2005065669 | 7/2005 |

OTHER PUBLICATIONS

Tao Zhengguo, "Fodder Pigment Production and Application", Edition 1, China Agricultural Science and Technology Publishing House, Sep. 2009, pp. 24-25 [English Abstract].
Mayne St. Beta-Carotene, carotenoids and disease prevention in humans. FASEB J. 10:690-701 (1996).
Report of a Joint WHO/FAQ Expert Consultation. Diet, Nutrition and the prevention of chronic disease. WHO technical report series, 916. Geneva, Jan. 28-Feb. 1, 2002. http://whqlibdoc.who.int/trs/who_trs_916.pdf.
Blanck HM, Gillespie C, Kimmons JE, Seymour JD, Serdula MK. Trends in fruit and vegetable consumption among US men and women, 1994-2005. Prev Chronic Dis. 5:2 (2008). http://www.cdc.gov/pcd/issues/2008/apr/07_0049.htm.
van het Hof KH, West CE, Westerate JA, Hautvast GAJJ. Dietary factors that affect the bioavailability of carotenoids. J Nutr. 130:503-06 (2000).
Maiani G, Cston MJP, Catasta G, Toti E, Cambrodon IG, Bysted A, Lorencia FG, et al. Carotenoids: Actual knowledge of food sources, intakes, stability and bioavailability and their protective role in humans. Mol Nutr Food Res. 53:S194-S218 (2009).
di Mascio P, Murphy ME, Sies H. Antioxidant defense systems: The role of carotenoids, tocopherols and thiols. Am J Clin Nutr 53:194S-200S (1991).
Bierer TL, Merchen NR, Erdman JW. Comparative absorption and transport of five common carotenoids in preruminant calves. J Nutr. 125:1569-1577 (1995).
Deshpande, J, et al, Novel Timed-Release Multicarotenoid Beadlets, Internet Publication (date unknown).
Cardinault N, Tyssandier V, Grolier P, Winklhofer-Roob B, Ribalta J, Bouteloup-Demange C, Rock E, Borel P; Comparison of the postprandial chlymicron carotenoid responses in young and older subjects. Eur J Nutr 42:315-323 (2003).
Johnson EJ, Qin J, Krinsky NI, Russell RM; Ingestion by men of a combined does of beta-carotene and lycopene does not affect the absorption of beta-carotene but improves that of lycopene. J Nutr 127:1833-1837 (1997).

(Continued)

*Primary Examiner* — John Pak
*Assistant Examiner* — Nathan W Schlientz
(74) *Attorney, Agent, or Firm* — Warner Norcross & Judd LLP (57) ABSTRACT

A controlled release beadlet that sequentially releases carotenoids over time within the gastrointestinal tract of a subject, as well as a method of administering the carotenoids. The beadlet provides a specific ratio of carotenoids which release from the beadlet at preselected times during passage through the gastrointestinal tract. The method includes releasing the carotenoids in preselected ratios at specific time intervals in the gastrointestinal tract to mitigate competition between the carotenoids for their uptake, and/or to potentially maximize the uptake of individual carotenoids within a mixed carotenoid formulation.

9 Claims, 4 Drawing Sheets

(56) References Cited

OTHER PUBLICATIONS

Murphy MM, Barraj LM, Herman D, Cheatham R, Randalph RK; Phytonutrient intake by adults in the Unites States in relation to fruit and vegetable consumption. J Acad Nutr Diet 112:222-229 (2012).

Omenn GS, Goodman GE, Thornquist MD, Balmes J, Cullen MR, Glass A, Keogh JP, Meyskens FL Jr, Valanis B, Williams JH Jr, Barnhart S, Cherniack MG, Brodkin CA, Hammar S; Effects of a combination of beta carotene and vitamin A on lung cancer and cardiovascular disease. N Engl J Med 334:1150-5 (1996).

O'Neill ME, Thurnham DI; Intestinal absorption of beta-carotene, lycopene and lutein in men and women following a standard meal: response curves in the triacylglycerol-rich lipoprotein fraction. Brit J Nutr 79:149-159 (1998).

Parker RS; Absorption, metabolism, and transport of carotenoids. FASEB J 10:542-551 (1996).

Tysandier V, Cardinault N, Caris-Veyrat C, Amiot M-J, Grolier P, Bouteloup C, Azais-Braesco V, Borel B; Vegetable-borne lutein, lycopene, and beta-carotene compete for incorporation into chylomicrons, with no adverse effect on the medium-term (3-wk) plasma status of carotenoids in humans. Am J Clin Nutr 75:526-34 (2002).

International Preliminary Report on Patentability including Written Opinion of the International Searching Authority for PCT/US2012/046658 dated Jan. 21, 2014.

Berg Van Der H: "Carotenoid Interactions", Nutrition Reviews, Allen Press, Lawrence, KS, US, vol. 57, No. 1, Jan. 1, 1999, pp. 1-10.

Van Den Berg Henk et al: "Effect of simultaneous, single oral doses of beta-carotene with lutein or lycopene on the beta-carotene retinyl ester responses in the triacylglycerol-rich lipoprotein fraction of men", American Journal of Clinical Nutrition, vol. 68, No. 1, Jul. 1998, pp. 82-89.

Nutrilite Health Institute: "America's Phytonutrient Report", Internet, 2010, pp. 1-14, Retrieved from the Internet: URL:http://www.nutrilite.com/en-us/Media/AmericaPhytonutrientReport.pdf [retrieved on Dec. 14, 2012].

PCT/US2012/046658 International Search Report, Jan. 30, 2013.

PCT/US2012/046658 Written Opinion, Jan. 30, 2013.

Yang, Wenping, et al, Advances of the Intestinal Absorption of Carotenoids, Research on Carotenoid Absorption, Journal of Domestic Animal Ecology, vol. 28, No. 6, Nov. 30, 2007 [English Abstract].

MULTICAROTENOID BEADLETS AND RELATED METHOD

BACKGROUND OF THE INVENTION

The present disclosure relates to dietary supplements and a method for administration, and more particularly, to beadlets having specific ratios of carotenoids which release in the gastrointestinal tract in a sequential, timed release manner.

Carotenoids are tetraterpenoid organic pigments that are naturally occurring in chloroplasts and chromoplasts of plants. Different types of carotenoids are known individually to promote skin health, eye health and prostate health, and to prevent free radical damage, among other things. For example, epidemiological studies over the last 30 years consistently demonstrate an inverse relationship between carotenoid-rich fruit and vegetable consumption and risk of chronic disease, such as heart disease, stroke and some types of cancer. Mayne S T. Beta-Carotene, carotenoids and disease prevention in humans. *FASEB J.* 10:690-701 (1996).

Human dietary intakes of fruits and vegetables, however, have been repeatedly found to be inadequate for optimal health. Report of a Joint WHO/FAQ Expert Consultation; Diet, Nutrition and the Prevention of Chronic Disease. *WHO Technical Report Series,* 916. Geneva, January 28-February 1 (2002); Blanck H M, et al. Trends in fruit and vegetable consumption among U.S. men and women, 1994-2005. *Prev Chronic Dis.* 5:2 (2008).

Therefore, there are a variety of supplements on the market that provide doses of carotenoids. These supplements suffer some issues. For example, supraphysiological doses of individual carotenoids have shown unexpected and worrisome results in the past, as in the case of β-carotene. Further, the effectiveness of a mixed carotenoid supplement is dictated by the fraction of the ingested amount that is actually absorbed and reaches its target site, also known as its "bioavailability." Much evidence suggests that, when administered together, individual carotenoids compete with one another for bioavailability, specifically for micelle formation and bile salts, which assist in uptake, and consequent intestinal absorption, thus limiting the efficacy of current multicarotenoids supplementation. van het Hof K H, et al. Dietary factors that affect the bioavailability of carotenoids. *J Nutr.* 130:503-06 (2000); Maiani G, et al. Carotenoids: Actual knowledge of food sources, intakes, stability and bioavailability and their protective role in humans. *Mol Nutr Food Res.* 53:S194-S218 (2009). For example, because β-carotene aggressively consumes bile salts, it is absorbed in the gastrointestinal tract more quickly, and reduces the absorption of other carotenes, such as lutein. Other carotenoids suffer similar competition issues, which impairs the effectiveness of conventional combination or mixed carotenoid supplementation.

SUMMARY OF THE INVENTION

A carotenoid formulation and related method that provide a combination of natural carotenoids which are present in a balanced and predetermined ratio, and which release in the gastrointestinal tract in a sequential, timed release manner to maximize the bioavailability of individual carotenoids by constraining competition for micelles and enteric uptake.

In one embodiment, the carotenoid formulation is in the form of a sequential, timed release multicarotenoid beadlet. The beadlet can include β-carotene, lutein, lycopene, α-carotene, zeaxanthin and optionally astaxanthin.

In another embodiment, the carotenoid formulation is formulated so that β-carotene, lutein, lycopene, α-carotene, zeaxanthin, and optionally astaxanthin are in a ratio of 12:6:4:2:1:1, respectively.

In still another embodiment, the β-carotene, lutein, lycopene, α-carotene, zeaxanthin, and optionally astaxanthin are formulated within an administration vehicle so that these carotenoids release from a beadlet or other administration vehicle into a human subject's gastrointestinal tract, e.g., the intestines, at 4-6 hours, 2-3 hours, 3-4 hours, 4-6 hours, 2-3 hours and 1-2 hours, respectively.

In even another embodiment, the β-carotene, lutein, lycopene, α-carotene, zeaxanthin, and optionally astaxanthin are formulated in a multilayered beadlet form. The beadlet includes a center and an exterior. From the center to the exterior, the carotenoids are layered or otherwise physically arranged in layers in the following order: β-carotene, α-carotene, lycopene, lutein, zeaxanthin, and optionally astaxanthin. Further optionally, the β-carotene and α-carotene may be combined in a single layer, and the lutein and zeaxanthin may be combined in a single layer.

In yet another embodiment, a method of supplementing a human diet is provided, the method comprising: providing a sequential, timed release multicarotenoid beadlet comprising β-carotene, lutein, lycopene, α-carotene, zeaxanthin, and optionally astaxanthin in a ratio of 12:6:4:2:1:1, respectively; and administering the beadlet to the human, so as to supplement the diet of the human. Optionally, the human can be deficient in carotenoids, and in need of such carotenoid supplementation.

In a further embodiment, the method can include releasing the β-carotene, α-carotene, lycopene, lutein, zeaxanthin, and optionally astaxanthin of the beadlet into a human subject's bloodstream at 4-6 hours, 4-6 hours, 3-4 hours, 2-3 hours, 2-3 hours and 1-2 hours, respectively, after administration of the multicarotenoid beadlet to the human.

The present invention is intended to provide a balanced carotenoid combination or mix, which separates the individual carotenoids within the intestinal tract, to minimize carotenoid uptake competition, improve bioavailability, and maximize effectiveness of the carotenoids. It is believed that the mixed carotenoid supplement, containing carotenoid ingredients at specific ratios, can be superior in balancing and elevating carotenoid intakes to match those recommended for a healthy diet. Further, such a sequential, timed released carotenoid formulation can potentially improve absorption across the intestinal wall, compared to that of conventional mixed carotenoid supplements of matching dosages of the carotenoids.

These and other objects, advantages, and features of the invention will be more fully understood and appreciated by reference to the description of the current embodiments and the drawings.

Before the embodiments are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DESCRIPTION OF THE CURRENT EMBODIMENTS

As discussed above, carotenoids compete with one another for absorption, thus limiting the efficacy of multicarotenoids supplementation. The current embodiments provide a combination carotenoid formulation that provides a mix of natural carotenoids in a balanced and desirable ratio; and incorporates a sequential, timed release formulation to maximize bioavailability of individual carotenoids by constraining competition for bile salts, micelles and consequent enteric uptake.

In the current embodiment of the carotenoid formulation, the carotenoids found in human plasma, which are associated with a variety of fruit and vegetable intake, are included. In particular, β-carotene, α-carotene, lutein, lycopene, zeaxanthin, and optionally astaxanthin are included in the carotenoid formulation. Each of these carotenoids are included at a preselected ratio which is derived by incorporating aspects of well-accepted dietary guidelines and considering widespread dietary inadequacies and imbalances. Specifically, results from Murphy, M M, et al, Phytonutrient intake by adults in the United States in relation to fruit and vegetable consumption. *J Acad Nutr Diet* 112:222-9 (2012), which utilized food consumption records collected as part of the USA National Health and Nutrition Examination Survey (NHANES), were used to systematically predetermine specific carotenoid intake in milligrams in a basic "prudent diet" of approximately five servings of fruit and vegetables per day. The balance of carotenoids found in a diet encompassing at least five servings of fruits and vegetables per day served as a goal amount of dosage for each carotenoid. The goal amounts of dosages, or predetermined daily intakes in milligrams, of β-carotene, α-carotene, lutein, lycopene, zeaxanthin, and optionally astaxanthin are presented in Table 1 below.

Using the above data as a baseline and goal amount, and then incorporating three factors: dietary guidelines for optimal health; the percentage of population not meeting the basic guidelines; and noted imbalances in the typical diet, that is, the heavy usage of tomato-based sauces for higher lycopene intake, a predetermined ratio of carotenoids was extrapolated to augment a typical consumer's carotenoid intake from red, yellow, and green pigmented fruits and vegetables. In some embodiments, astaxanthin was chosen for its health benefits in addition to the fact that very few diets consist of astaxanthin-rich food sources.

It is believed that the above extrapolated predetermined ratio of carotenoids, incorporated into the multicarotenoid formulation, when consumed, will convert an unbalanced and inadequate carotene intake of a "typical" diet into a more balanced and ideal amount in a prudent diet. As such, a typical user of this supplement can receive a ratio of carotenoids estimated to be found in the recommended diet containing at least five servings of red, yellow, and green-pigmented fruits and vegetables per day, in effect meeting a "goal" ratio of carotenoids, which is shown below in Table 1.

TABLE 1

Carotenoid Formulation Daily Intake, Ratios, and Release Profiles

| Carotenoid | Predetermined Daily Intake (mg) | Preselected Dosage Ratio | Sequential Release Profile into the Gastrointestinal Tract (hours) |
|---|---|---|---|
| β-carotene | 6 | 12 | 4-6 |
| α-carotene | 3 | 2 | 4-6 |
| Lycopene | 2 | 4 | 3-4 |
| Lutein | 1 | 6 | 2-3 |
| Zeaxanthin | 0.5 | 1 | 2-3 |
| Astaxanthin | 0.5 | 1 | 1-2 |

Supplementation with synchronous carotenoids presents the challenge of competition with one another for uptake within the enteric system. There is much interaction between various individual carotenoids during micelle formation and perhaps during receptor mediated uptake resulting in the inhibition of uptake of one over the other. van het Hof K H, et al. Dietary factors that affect the bioavailability of carotenoids. *J Nutr.* 130:503-06 (2000); Maiani G, et al. Carotenoids: Actual knowledge of food sources, intakes, stability and bioavailability and their protective role in humans. *Mol Nutr Food Res.* 53:S194-S218 (2009). To mitigate such competition and potentially maximize uptake of individual carotenoids from a multicarotenoid formulation, the current embodiment of the combination carotenoid formulation is implemented in a layered multicarotenoid beadlet that sequentially releases individual carotenoids over the transit time of approximately 6 hours within the upper intestinal system of the human gut. The sequence of release of the individual carotenoids was designed to match the sequence by which each carotenoid first appears in the triacylglycerol rich fraction of plasma after oral administration.

Incidentally, the sequence design also is generally the opposite of and contradicts the teachings of others who have attempted carotenoid formulations. For example, certain manufacturers have designed multicarotenoid formulations to release carotenoids based on their affinity to bile salts. Indian Patent Application Publication 2181/MUM/2007, entitled Novel Timed-Release Multicarotenoid Composition and a Process for Its Preparation, filed Jan. 11, 2007, which is hereby incorporated by reference, discloses that carotenoids having greater affinity toward bile salts, for example β-carotene, are released immediately upon administration, while carotenoids having lesser affinity toward bile salts, such as lutein, are released well after administration, to reduce the competition for bile salts and facilitate absorption of those individual carotenoids.

Optionally, the multicarotenoid beadlet of the current embodiments can be administered to a human or other subject who is identified as being deficient in carotenoids. For example, a subject can undergo conventional testing to assess whether the subject is consuming a level of carotenoids that meet certain goal amounts of dosages as noted above. If not, then the multicarotenoid beadlets can be administered to correct the deficiency.

Figure 1:
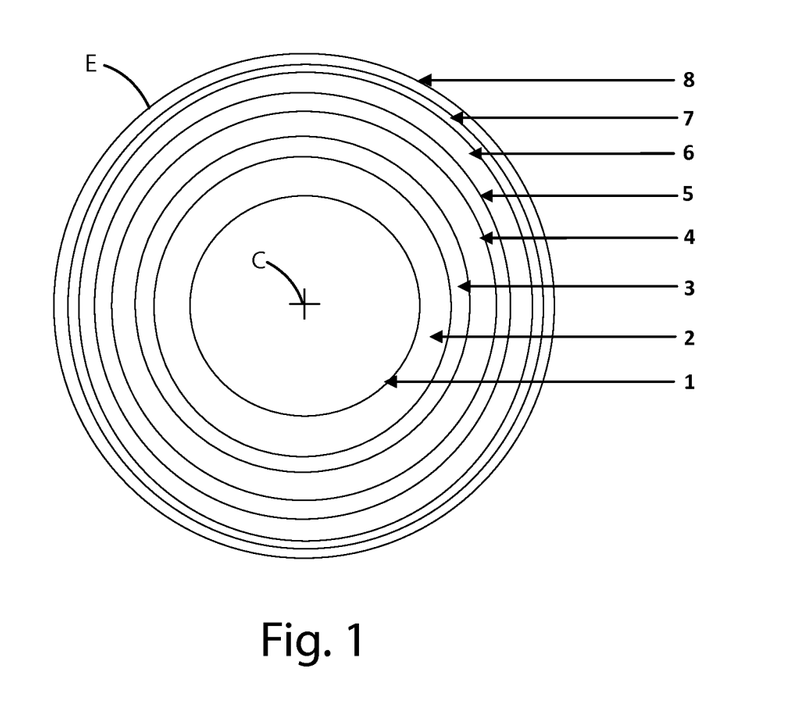
FIG. 1 is a cross section view of a first embodiment of a controlled release beadlet of the current embodiment.

Returning to the vehicle for administration, FIG. 1 illustrates a sequential, timed release or controlled release multicarotenoid beadlet design of the current embodiment. Values for selected intakes and dosage ratios of carotenoids contained in this beadlet are provided in Table 1 above; however, these values may vary from the recited values up to about +/−5%, +/−10%, or +/−20%, for one or more of the carotenoids. Further, as noted above, astaxanthin is optional. Therefore, in some embodiments the astaxanthin might not be included. In addition, Table 1 above provides a sequential release schedule of the multicarotenoids beadlet of the current embodiment; however, there may be some variation in the time release of one or more of the carotenoids, depending on the application, beadlet design and dosage.

The beadlet in FIG. 1 is prepared in a layered form. The layers are sequenced from the core C to the exterior surface E so that as the beadlet passes through the gastrointestinal tract, for example, the upper digestive tract, the layers are slowly eroded by gastrointestinal fluids and absorption with the erosion of the beadlet, proceeding from the exterior surface E to the interior core C. With this type of erosion and subsequent absorption, the carotenoids in the layers are exposed to and can be absorbed in the gastrointestinal tract in the desired sequence at the desired times.

As shown below in Table 2, the layers 1-8 of the beadlet in FIG. 1, from exterior E toward the core C, are positioned or disposed in ordered physical locations, for example, within separate and distinct layers, so that the carotenoids are released in the order (first to last release): astaxanthin, lutein, zeaxanthin, lycopene, β-carotene and α-carotene.

TABLE 2

Controlled Release Beadlet Layers and Release Profiles

| Ref. No. | Layer (or coating) | Release Profile |
|---|---|---|
| 1 | NPS/Sugar sphere (#60-80) | |
| 2 | β-carotene (*Dunaliella* algae) + α-carotene (palm) coat | 4-6 hrs |
| 3 | Functional coat-I (ethyl cellulose + Eudragit E100 followed by ethyl cellulose) | |
| 4 | Lycopene (tomato) coat | 3-4 hrs |
| 5 | Lutein and zeaxanthin (marigold) coat | 2-3 hrs |
| 6 | Functional coat-II (enteric Coating with Eudragit L30D55) | |
| 7 | Astaxanthin (*Haematococcus* algae) coat | 1-2 hrs |
| 8 | Functional coat-III (HPMC E-5) | |

Optionally, the different layers 1-8 can include intermixed carotenoids so that those carotenoids are released nearly simultaneously when the respective layer including the two or more intermixed carotenoids is exposed upon degradation within the gastrointestinal tract. For example, layer 2 can include β-carotene and α-carotene, and layer 5 can include lutein and zeaxanthin. These different subsets of carotenoids can be combined based on their common desired release profile within the gastrointestinal tract and/or compatibility as presented in Table 2 above.

Further optionally, the physical location of specific carotenoids within the beadlet in relation to the exterior surface E and/or core C can be selected so that specific carotenoids are exposed to and initially released in the gastrointestinal tract. For example, the lutein and zeaxanthin can be positioned closer to the exterior surface E than the β-carotene and/or α-carotene so that the gastrointestinal fluids within the gastrointestinal tract dissolve and generally remove portions of the beadlet to expose the lutein and zeaxanthin ingredients and/or materials well before the β-carotene and/or α-carotene is exposed to those fluids and able to be initially released into the gastrointestinal tract. By initially released, it is meant that the particular carotenoids are satisfactorily exposed by degradation, erosion and/or dissolution of the various layers of the beadlet so that the carotenoids are released into the gastrointestinal tract in a manner so that they are capable of being absorbed therein and eventually making their way into the bloodstream of the subject.

In the embodiment illustrated in FIG. 1, for example, the lutein and/or zeaxanthin can be exposed to and initially released in the gastrointestinal tract from a beadlet before the β-carotene is exposed to and initially released into the gastrointestinal tract from a beadlet. These ingredients, lutein and/or zeaxanthin can also be exposed and released into the gastrointestinal tract before the α-carotene is exposed to and initially released into the gastrointestinal tract from a beadlet. Likewise, the lycopene can be exposed to and initially released into the gastrointestinal tract before the β-carotene and/or α-carotene. Further, lycopene can be exposed to and initially released into the gastrointestinal tract after the lutein and/or zeaxanthin are exposed to and initially released therein from the beadlet. In addition, the optional astaxanthin can be exposed to and initially released into the gastrointestinal tract before the lutein, zeaxanthin, lycopene, β-carotene and/or α-carotene are exposed to and initially released from the beadlet.

The particular carotenoids used in the beadlet construction can come from a variety of sources. For example, β-carotene can be obtained from *Dunaliella* algae, as well as variety of fruits and vegetable extracts and/or powders, such as mango, carrots, pumpkin, papaya, peaches, prunes, sweet potato, apricots, lima beans, green beans, broccoli, brussel sprouts, kale, kiwi, lettuce, peas, spinach, tomatoes, pink grapefruit, honeydew melon, oranges and certain yeasts. The α-carotene can be obtained from palm, as well as a variety of fruits and vegetable extracts and/or powders such as sweet potatoes, apricots, pumpkin, green beans, lima beans, broccoli, brussel sprouts, kale, kiwi, lettuce, peas, spinach, prunes, peaches, mango, papaya and carrots. Lycopene can be obtained from tomatoes, as well as a variety of fruits and vegetable extracts and/or powders such as watermelons, pink grapefruit, apricots, guavas and certain yeasts. Zeaxanthin can be obtained from marigold, as well as a variety of fruits and vegetable extracts and/or powders such as peaches, spinach, collards, oranges, papaya, prunes, pumpkin, mango, kale, kiwi, lettuce, honeydew melon and yellow corn. Lutein can be obtained from marigold, as well as a variety of fruits and vegetable extracts and/or powders such as mango, papaya, oranges, kiwi, peaches, peas, lima beans, green beans, broccoli, brussel sprouts, kale, lettuce, prunes, pumpkin, sweet potatoes and honeydew melon. Astaxanthin can be obtained from *Haematococcus* algae, as well as a variety of other sources such as krill, plankton, salmonids and certain yeasts.

As further shown in FIG. 1, the beadlet can include multiple additional optional layers and ingredients generally included in the multicarotenoid formulation. For example, the layer 8 adjacent or forming the exterior E can be a functional coating. One example is a hydroxypropylmethylcellulose (HPMC) coating. Layer 6 can be a functional coating that can promote absorption of the respective carotenoids, for example, an enteric coating including Eudragit® L30D55, commercially available from Evonik Industries AG of Germany. Layer 3 can be another functional coating, for example, a layer containing Eudragit® E100 sandwiched between layers of ethylcellulose. Layer 1, which generally forms an optional solid center of the beadlet can be a sugar or other enteric absorbable material.

Although not shown, each layer of the beadlet and/or the beadlet as a whole can include a variety of stabilizers, coating polymers, fillers, binders, excipients, bioenhancer absorption aids, flavors and/or preservatives depending on the application.

The multicarotenoid formulation of the current embodiment is illustrated in, but not intended to be limited by, the following examples.

Example 1

Figure 2:
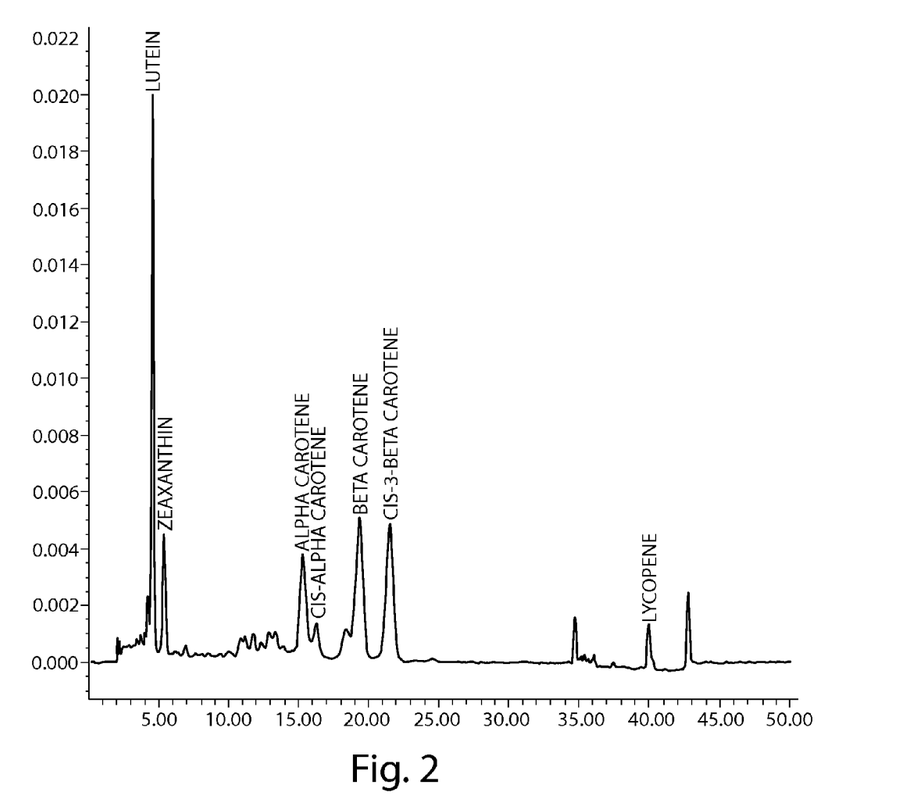
FIG. 2 is a representative chromatogram of the first embodiment of the controlled release beadlet.

Multicarotenoid beadlets having the multiple layer construction described above in connection with FIG. 1, and the constructions shown in Table 1, or other constructions as described below, were prepared and then tested for dissolution. FIG. 2 illustrates a representative chromatogram of such a sequential, timed release beadlet. The protocol to obtain this data is described in Table 3 and further below.

TABLE 3

| Dissolution Parameters and Procedure | |
|---|---|
| Dissolution medium volume | 500 ml |
| Type | USP Type II Paddle |
| RPM | 100 |
| Temperature | 37° C. +/− 0.5° C. |
| Time Intervals | 2 hrs in 0.1N HCl, continued with 6 hrs in pH 6.8 buffer with 1.5% SLS |
| Sampling Time | Hourly for 8 hours |
| Aliquots Volume | 20 ml |
| Aliquots replenish volume | 20 ml |
| Beadlet quantity | 700 mg |

The above aliquots of beadlet samples in Table 3 were subjected to a high performance liquid chromatography (HPLC) analysis. The standard for the HPLC analysis was β-carotene, Type II Synthetic, Sigma Aldrich, Cat #C4582-25MG, Lot #120M5165V, Purity: 99.840%, available from Sigma Aldrich of St. Louis, Mo. All values reported are relative to the β-carotene standard, however, astaxanthin analysis used a different method.

To prepare the samples, for each 20 mL dissolution aliquot, 10 mL of extraction solution and 2 g of sodium chloride was added to the sample. The sample was then placed on a shaker for 15 minutes and then centrifuged at 3000 rpm for 5 minutes. Approximately 1.5 mL of the uppermost layer was then transferred to an HPLC vial for analysis.

Conditions for the HPLC used in this example were as follows. The column was a YMC Carotenoid (C-30), 5.0 μm, 4.6×250 mm, P/N CT99S052546WT, S/N 13363114313006, available from YMC Co. Ltd. of Kyoto, Japan. The mobile phase was Channel C: 80/20 Methanol/Chloroform Channel D: 50/50 Methanol/Chloroform. The flow rate was 1.5 mL/min, Injection: 10 μL, Run Time 50 min., 30° C. The analytical wavelengths were 474 and 454 nm. The gradient was that as shown in Table 4 below.

TABLE 4

| Gradient for HPLC | | |
|---|---|---|
| Time | % C | % D |
| 0.0 | 100 | 0 |
| 20.0 | 100 | 0 |

TABLE 4-continued

| Gradient for HPLC | | |
|---|---|---|
| Time | % C | % D |
| 32.0 | 100 | 0 |
| 32.1 | 0 | 100 |
| 40.0 | 0 | 100 |
| 40.1 | 100 | 0 |
| 50.0 | 100 | 0 |

FIG. 2 shows the representative chromatogram of the sequential, timed release beadlet including β-carotene, lutein, lycopene, α-carotene and zeaxanthin from the above HPLC analysis.

Example 2

Figure 3:
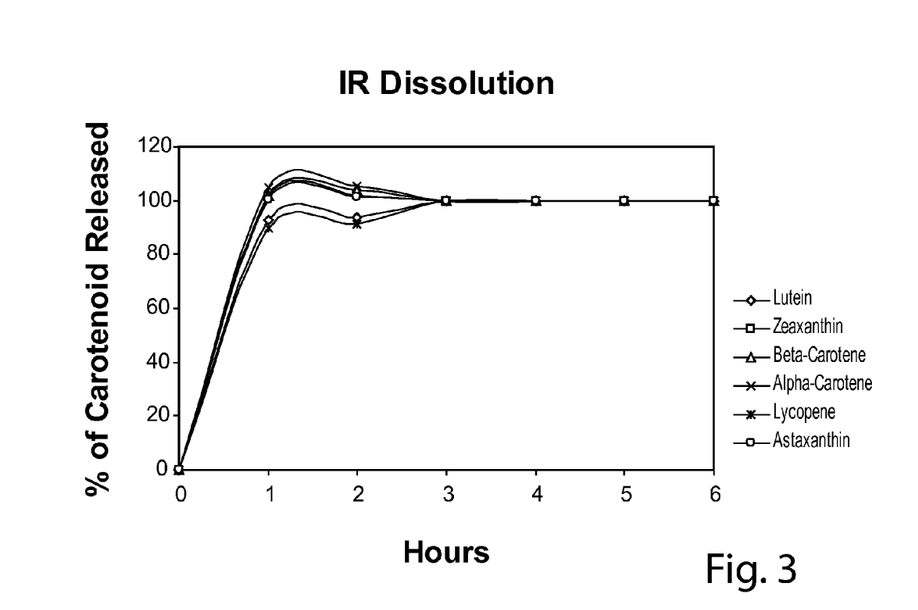
FIG. 3 is a chart illustrating a dissolution profile of an immediate release beadlet design.
Figure 4:
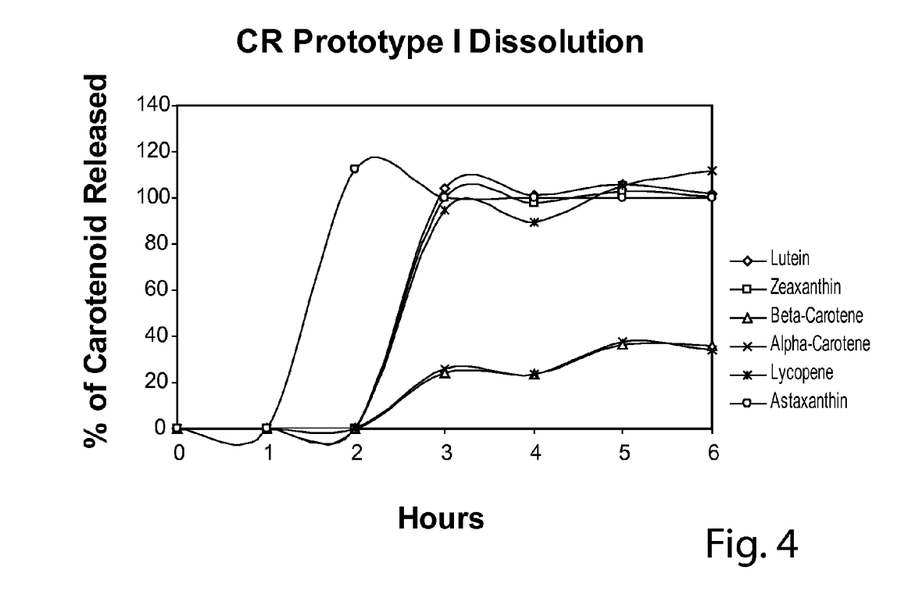
FIG. 4 is a chart illustrating a dissolution profile of a second embodiment of a controlled release beadlet (Prototype I).
Figure 5:
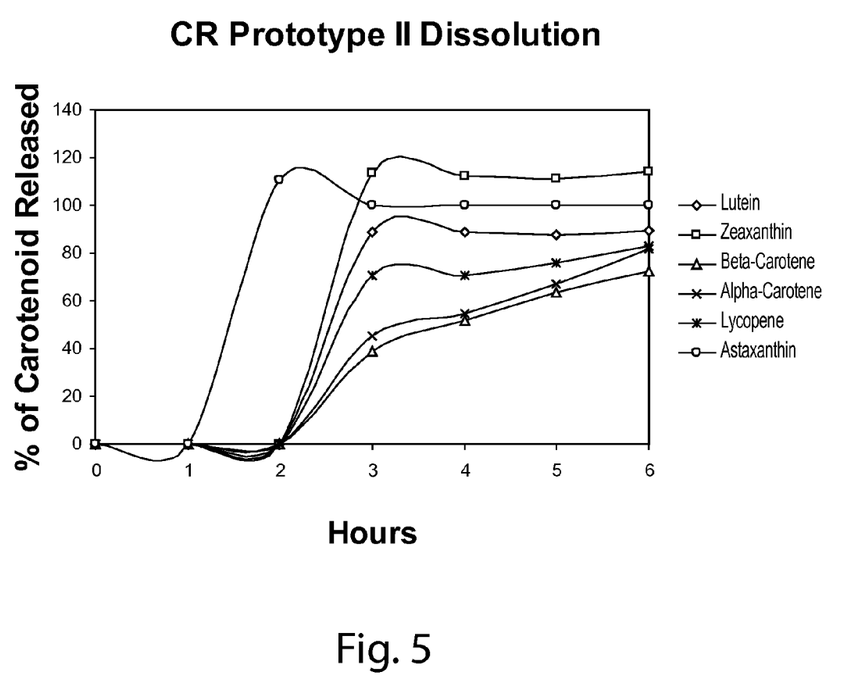
FIG. 5 is a chart illustrating a dissolution profile of a third embodiment of a controlled release beadle (Prototype II).

In this example, the carotenoid composition of an immediate release (IR) multicarotenoid formulation, that is, one where individual carotenoids are not layered and not released sequentially, but instead, released all simultaneously, was compared to two embodiments of sequential, timed release, also referred to as controlled release (CR), multicarotenoid beadlets. The precise amounts of the respective carotenoids from each formulation are represented in milligrams per gram (mg/g) in Table 5 below. FIGS. 3-5 illustrate the dissolution profiles of the immediate release (IR) beadlet (FIG. 3) and two embodiments of controlled release (CR) beadlets, referred to as Prototype I (FIG. 4) and Prototype II (FIG. 5). As illustrated, there is a difference in release of β-carotene and α-carotene between Prototypes I and II.

TABLE 5

| Composition of Immediate (IR) and Controlled Release (CR) Beadlets (mg/g) | | | |
|---|---|---|---|
| | IR Prototype | CR Prototype 1 | CR Prototype 2 |
| β-carotene | 34.30 | 16.34 | 18.83 |
| Lutein | 20.73 | 8.80 | 10.52 |
| Lycopene | 10.49 | 5.83 | 5.34 |
| α-carotene | 4.79 | 3.10 | 3.35 |
| Zeaxanthin | 5.13 | 2.52 | 2.28 |
| Astaxanthin | 1.57 | 1.50 | 1.53 |

Based on the above information, it was concluded that it is possible to adjust the formulation and modify the release pattern as between the sequential, timed release Prototypes I and II, and a variety of other multicarotenoid formulations. Further modification should also completely release all carotenoids in the controlled release formulation. These in vitro dissolution experiments demonstrated significant temporal separation of carotenoid release, for example, the β-carotene, α-carotene, lycopene, lutein, zeaxanthin, and optionally astaxanthin being sequentially released in the intervals as noted above. The data also support a clinical comparison of immediate and controlled release formulations in a human population to confirm the effect on carotenoid bioavailability in vivo.

Example 3

A clinical study comparing immediate release multicarotenoid formulations and controlled release multicarotenoid formulations will be performed. This clinical study will be designed based on the following. Within the intestinal tract, carotenoids form into multilamellar lipid vesicles, those mixed lipid micelles composed of bile salts, free fatty acids, monoglycerides and phospholipids. Once formed into micelles, carotenoids are generally considered to be absorbed into duodenal mucosal cells by passive diffusion. The rate of diffusion is determined by a concentration gradient between the micelle and the enterocyte. Carotenoids are transported from the intestinal mucosa to the blood stream exclusively by the chylomicrons. This provides a convenient compartment type model, with which to assess carotenoid uptake after consumption.

Thus, in the study, the post-prandial chylomicron fractions of the plasma will be assessed to determine the uptake after release from the vehicle of two different formulations of mixed carotenoid capsules. Further, data suggests that individuals absorb carotenoids in a very specific, individualized manner when measured over time, so the study will implement a repeated measure design where each subject takes two different types of products, that is, an immediate release multicarotenoid formulation and a controlled release multicarotenoid formulation, in a randomized order in an effort to reduce inter-subject error.

It is believed that, when tested in the same subject, sequentially releasing carotenoids in the intestinal tract will decrease competition and result in increased absorption of the above-noted six individual carotenoids over the absorption seen following the intake of a similarly matched-dose, conventionally-released multicarotenoid product.

In particular, the primary objective of the study will be to compare the bioavailability of a sequential timed released mixed carotenoid capsule to a matched-dose, conventional mixed carotenoid capsule. As a standard of practice, the general safety of the mixed carotenoid product will also be evaluated. All doses of carotenoids included within the study will be well within normal, healthy ranges of supplementation.

Efficacy will be assessed through post-prandial serial plasma samples analyzed for each individual carotenoid extracted from the chylomicron and triacylglycerol-rich fraction of the blood. Carotenoid concentrations will be expressed in incremental responses with fasting baseline values being set to zero. The area under the curve (AUC) of each carotenoid will be calculated using the trapezoidal rule. Carotenoid AUC's obtained in the two subject groups (SRC and CRC) will be compared using a repeated measure analysis of variance (ANOVA).

Safety and tolerability will also be assessed throughout the study by measuring change from baseline in each of the following: serum chemistry, serum hematology, urinalysis, vital signs, body weight, and subject-reported adverse events.

The study designed is a pilot trial of 4 human subjects, to test the sensitivity of the study design and laboratory analysis. These 4 subjects will be provided a single dose of a sequential-released capsule (SRC Dose A) or a matched-dose, conventional-released capsule (CRC Dose A) in a random, cross-over pattern, 14 days apart. With the study completed, plasma samples of each subject will be analyzed for post-prandial carotenoid status.

It is anticipated that carotenoids will be detected in these plasma samples, in which case the study Phase I will continue with Phase II-A; however, if carotenoids are not detected within these plasma samples, the study Phase I will continue with Phase II-B. Both outcomes are described in greater detail below.

Phase II-A: If carotenoids are detected in the plasma samples from Phase I, indicating adequate test sensitivity, the study will continue with Phase II-A. In the event that this is the determined study direction, 8 additional subjects will be recruited and follow the same study procedure as Phase I. These 8 subjects will be provided with SRC Dose A or CRC Dose A in a random, cross-over pattern, 14 days apart.

Phase II-B: In the event that carotenoids are not detected in the plasma samples from Phase I, perhaps indicating Dose A may be too low to be measured within the triacylglycerol rich fraction of the blood, the study will continue with Phase II-B. In the event that this is the determined study direction, 12 additional subjects will be recruited and follow the same study procedure as Phase I, but with a slightly higher supplement dose to increase sensitivity of plasma analysis. These 12 subjects will be provided with SRC Dose B or CRC Dose B in a random, cross-over pattern, 14 days apart. The particular dose specifics for Dose A and Dose B are presented in Table 6 below.

After consenting to be in the study, each subject is screened for abnormalities in vital signs, lipid panel, serum chemistry, hematology, and urinalysis following submission of a maximum 25 ml blood draw and a minimum 7 ml urine sample, approximately 3 days prior to the start of the study (Visit 1). Subjects will be instructed to maintain their normal diet and exercise habits throughout the duration of the study, with the exception of being asked to avoid consuming any high-carotenoid fruits and vegetables within the 3 days prior to each visit. Subjects will be verbally instructed and provided with a list of foods to avoid for this time frame. Subjects will be instructed to fast for 12 hours prior to each appointment day.

On the day of testing (Visit 2), each qualified subject will be given a brief dietary recall questionnaire to assess consumption history of carotenoid containing foods. After assessment for compliance on the 12 hour fasting requirement, a baseline fasting blood sample will be taken, followed by an allotted 20 minutes for consumption of a standardized, carotenoid-free study meal and the assigned swallowable mixed carotenoid capsule at Dose A or Dose B (depending on Phase of study, see below). Serial blood draws will be taken at baseline as well as 1, 2, 4, 6, and 8 hours after time of product consumption.

Fourteen days later (Visit 3), the subjects will repeat the procedure, in a repeated-measure crossover design, so each subject received the opposite matched dose formulation as the experiment prior. Following the last postprandial blood draw, at the conclusion of the study, each subject will be again screened for abnormalities in serum chemistry, hematology, and urinalysis for safety measures.

All active ingredients will be derived from natural sources and combined with excipients and fillers to form the carotenoid beadlets, and standard excipients will be used to make CRC and SRC capsules that are matched in weight, color and size to maintain blinding. The active ingredients used in both CRC and SRC capsules will be as follows: β-carotene (*Dunaliella* algae and palm fruit), α-carotene (palm fruit), lutein (marigold), zeaxanthin (marigold), lycopene (tomato) and astaxanthin (*Haematococcus* algae). Inert ingredients will be as follows: hydroxypropyl methylcellulose, ethyl cellulose, sucrose, methacrylic acid, talc (purified), mixed natural tocopherols, ascorbyl palmitate, silica, sodium starch glycolate, microcrystalline cellulose.

TABLE 6

Dose of Mixed Carotenoids to be Provided to Subjects

| | Phase I/II Dose A (mg) | | Phase II Dose B (mg) | |
|---|---|---|---|---|
| | Dose A: CRC (3 capsules) | Dose A: SRC (3 capsules) | Dose B: CRC (4 capsules) | Dose B: SRC (4 capsules) |
| β-carotene | 24.00 | 24.00 | 36.00 | 36.00 |
| Lutein | 12.93 | 13.18 | 19.39 | 19.78 |
| Lycopene | 7.39 | 9.43 | 11.08 | 14.14 |
| α-carotene | 4.89 | 5.11 | 7.33 | 7.67 |
| Zeaxanthin | 2.50 | 2.94 | 3.74 | 4.41 |
| Astaxanthin | 2.00 | 2.00 | 3.00 | 3.00 |
| Total Active Weight | 53.71 | 56.66 | 80.54 | 85.00 |
| Total Weight (with excipients) | 1394.4 | 1247.4 | 1751.4 | 2091.6 |

As noted in Table 6 above, in Phase I/II: Dose A, the matched non-sequential release placebo capsule (CRC) will be composed of 1310 mg of sequential-release multicarotenoid beadlets+84.4 mg of astaxanthin beadlets, for a total weight of 1394.4 mg in a single dose of 3 capsules. In Phase II: Dose B, the SR multicarotenoid capsule (SRC) will be composed of 1965 mg of multicarotenoid beadlets+126.6 mg of astaxanthin beadlets, for a total weight of 2091.6 mg in 4 capsules. The respective carotenoids doses in each of Dose A and Dose B are also presented in Table 6 above.

In Phase I/II: Dose A, the sequential release multicarotenoids (SRC) will be composed of 923 mg of multicarotenoid beadlets+84.4 mg of astaxanthin beadlets, for a total weight of 1007.4 mg. To maintain blinding, 240 mg of microcrystalline cellulose, a standard binder used in supplements, will be added to the formula to achieve the matched three capsule dose.

In Phase II: Dose B of the matched non-sequential release control capsule (CRC) will be composed of 1385 mg of multicarotenoid beadlets+126.6 mg of Astaxanthin beadlets, for a total weight of 1511.6 mg. To maintain blinding, the matched four capsule dose will be achieved by adding 240 mg of microcrystalline cellulose, a standard binder used in supplements.

The study in this example will be a repeated-measure crossover trial. Each subject will receive both the experimental sequential release (SRC) and matched-dose conventional (control-CRC) capsules in random order. The product order will be blinded to the subject and blinded to the investigator.

During the trial subjects will follow their usual diets, with the exception of avoiding high carotenoid foods for 3 days prior to each visit and arriving to the testing center on the day of experiment following an overnight fast. At the beginning of each visit, the experimental or control capsule will be assigned to each subject to consume along with a standardized carotenoid-free study meal. Phase I of the study will entail the carotenoid profile in Dose A (below). Phase II will entail subjects being given either Dose A (Phase II-A) or Dose B (Phase II-B), depending on the outcome of the sensitivity assessments of plasma chylomicrons in Phase I.

Absorption will be assessed through post-prandial serial plasma samples analyzed for each individual carotenoid extracted from the chylomicron and triacylglycerol-rich fraction of the blood. Several different statistical methods will be used to analyze the data. Carotenoid concentrations will be expressed in incremental responses with fasting baseline values being set to zero. The maximum delta score for each carotenoid will be calculated and the summation of each carotenoids delta score (Z-score of deltas) will be compared between the two formulations. The Area Under the Curve (AUC) of each carotenoid will be calculated using the trapezoidal rule. Carotenoid AUCs obtained in the two experimental groups (SRC and CRC) will be compared using a paired T-test. ANOVA method will be utilized to evaluate for interaction effects of time and formulation type on the outcome variable of plasma carotenoid levels.

It is believed that the above study will support several conclusions. First, the total area under the curve, calculated over an 8 hour post-prandial period will be greater after the consumption of the sequentially-released multicarotenoid than after a similarly-matched dose of conventional simultaneous release multicarotenoid product in at least three of the six individual carotenoids. Further, the maximum change from baseline (delta score) will be greater after consumption of the sequentially-released multicarotenoid than after a similarly matched dose of conventional simultaneous release multicarotenoid product in at least three of the six individual carotenoids. Additionally, the summation of all delta scores (Z-score of deltas) will be greater following the consumption of the sequentially-released multicarotenoid than after the similarly-matched dose of the conventional simultaneous release product. There also should be a significant interaction effect between time and formulation on the outcome variable of plasma chylomicron measure of specific carotenoids after statistical assessment. It is believed that the items above will further support improved bioavailability of a sequential-released multicarotenoid product over a similarly-matched dose of a simultaneous release multicarotenoids product.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to packages of any specific orientation(s).

All patents, patent applications, and literature references cited in this specification are hereby incorporated herein by reference in their entirety. In case of conflict, the present description, including definitions, will control.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular. Any reference to claim elements as "at least one of X, Y and Z" is meant to include any one of X, Y or Z individually, and any combination of X, Y and Z, for example, X, Y, Z; X, Y; X, Z; and Y, Z.

The embodiments of the invention in which an exclusive property or privilege is claimed are defined as follows:

1. A method of supplementing a human diet comprising:
    providing a formulation comprising carotenoids: β-carotene, lutein, lycopene, α-carotene and zeaxanthin,
    administering the formulation to a human, and
    sequentially releasing the carotenoids within the gastrointestinal tract of the human so that the β-carotene and α-carotene are released into the gastrointestinal tract of the human after the lycopene, which is released into the gastrointestinal tract of the human after the lutein and zeaxanthin.

2. The method of claim 1 wherein the formulation is in the form of a multilayered beadlet including a core and an exterior, wherein the at least one of the β-carotene and α-carotene is disposed in a layer that is closer to the core than another separate and distinct layer including at least one of the lutein and zeaxanthin.

3. The method of claim 1 wherein the β-carotene, lutein, lycopene, α-carotene and zeaxanthin are present in a weight ratio of 12:6:4:2:1, respectively.

4. The method of claim 1, wherein the carotenoids further comprise astaxanthin, wherein the astaxanthin is released into the gastrointestinal tract of the human prior to the lutein and zeaxanthin.

5. The method of claim 4 wherein the β-carotene, lutein, lycopene, α-carotene, zeaxanthin and astaxanthin are present in a weight ratio of 12:6:4:2:1:1, respectively.

6. The method of claim 1 wherein the carotenoids further comprise astaxanthin, wherein the astaxanthin releases from the formulation into the gastrointestinal tract of the human 1 hour to 2 hours after the administering step.

7. The method of claim 1 wherein the β-carotene and α-carotene release from the formulation into the gastrointestinal tract of the human 4 hours to 6 hours after the administering step.

8. The method of claim 7 wherein the lutein and zeaxanthin release from the formulation into the gastrointestinal tract of the human 2 hours to 3 hours after the administering step.

9. The method of claim 8 wherein the lycopene releases from the formulation into the gastrointestinal tract of the human 3 hours to 4 hours after the administering step.

* * * * *